(12) United States Patent
Kalies

(10) Patent No.: US 8,346,570 B2
(45) Date of Patent: Jan. 1, 2013

(54) METHOD FOR IMPROVING THE CONSISTENCY OF PROCESSING PHARMACY DATA

(75) Inventor: Ralph F. Kalies, Pickett, WI (US)

(73) Assignee: Omnicare, Inc., Covington, KY (US)

( * ) Notice: Subject to any disclaimer, the term of this patent is extended or adjusted under 35 U.S.C. 154(b) by 2160 days.

(21) Appl. No.: 10/756,608

(22) Filed: Jan. 13, 2004

(65) Prior Publication Data
US 2004/0148198 A1    Jul. 29, 2004

Related U.S. Application Data

(60) Provisional application No. 60/439,758, filed on Jan. 13, 2003.

(51) Int. Cl.
*G06Q 10/00* (2006.01)
(52) U.S. Cl. ............................................. 705/2
(58) Field of Classification Search ............ 705/2–3
See application file for complete search history.

(56) References Cited

U.S. PATENT DOCUMENTS

| | | | |
|---|---|---|---|
| 3,970,996 A | 7/1976 | Yasaka et al. | |
| 5,359,509 A | 10/1994 | Little et al. | |
| 5,704,044 A | 12/1997 | Tarter et al. | |
| 5,737,539 A * | 4/1998 | Edelson et al. | 705/3 |
| 5,758,095 A | 5/1998 | Albaum et al. | |
| 5,845,255 A | 12/1998 | Mayaud | |
| 5,950,630 A * | 9/1999 | Portwood et al. | 128/897 |
| 6,067,524 A | 5/2000 | Byerly et al. | |
| 6,223,164 B1 | 4/2001 | Seare et al. | |
| 6,266,645 B1 | 7/2001 | Simpson | |
| 6,356,873 B1 | 3/2002 | Teagarden et al. | |
| 7,069,226 B1 * | 6/2006 | Kleinfelter | 705/2 |
| 2002/0029223 A1 | 3/2002 | Rice et al. | |
| 2002/0035484 A1 | 3/2002 | McCormick | |

FOREIGN PATENT DOCUMENTS

| | | |
|---|---|---|
| WO | 01/71641 | 9/2001 |
| WO | 02/052483 | 7/2002 |
| WO | 02/084560 | 10/2002 |

* cited by examiner

*Primary Examiner* — Robert Morgan
*Assistant Examiner* — Rajiv Raj
(74) *Attorney, Agent, or Firm* — Ostrolen Faber LLP

(57) ABSTRACT

A method for consistent processing of pharmacy data. An order for a prescription is transmitted from a healthcare facility to a pharmacy. The pharmacy transmits a claim relating to the order from the pharmacy to a processing center. The processing center reviews the claim according to predetermined claim criteria and either accepts the claim if it conforms to the claim criteria or rejects the claim if it does not conform to the claim criteria. The processing center transmits one of an approval notification and a rejection notification to the pharmacy. For rejected claims, the processing center transmits at least one basis for the rejection to the pharmacy. The pharmacy corrects the non-conforming portion of the claim, then transmits the corrected claim to the processing center. The claim review and approval or rejection steps are then repeated until the claim conforms to the predetermined claim criteria.

4 Claims, 2 Drawing Sheets

METHOD FOR IMPROVING THE CONSISTENCY OF PROCESSING PHARMACY DATA

This application claims priority to U.S. provisional application 60/439,758, filed Jan. 13, 2003, the contents of which are hereby incorporated by reference.

FIELD

This invention relates to a method for processing pharmacy data. Specifically, the invention relates to a method for processing pharmacy data using an electronic network as a communications medium.

BACKGROUND

In the past, healthcare plans placed few restrictions on their subscribers' health care choices, such as selecting physicians and pharmacies. Health care was generally provided by individual physicians acting independently. Likewise, patients receiving prescriptions from their physicians typically had them filled at an independently operated pharmacy. The health care system has undergone radical change in recent years as a result of pressures to contain costs and increase profitability. Most health care plans are now administered by managed care organizations ("MCOs"). Under the MCO system much of the decision-making power is shifted from the healthcare provider to an administrative function within the managed care organization. MCOs establish standards of care, standardize methods of delivering care, and evaluate the care given.

Similarly, many pharmacies have migrated from independent operations to regional and national networks of Publicly-held Corporate Pharmacies ("PCPs"). This paradigm shift is due to a desire by the industry to minimize the cost of drug therapy and to maintain profitability. The MCOs have driven much of this trend by entering into agreements with pharmacy networks to obtain advantages such as volume discounts, then providing economic incentives such as reduced co-payment requirements for plan subscribers who purchase their prescriptions at the preferred pharmacies. Thus, joining a pharmacy network has become an economic necessity for the economic survival of numerous independent pharmacies, many of whom have seen their market share erode as a result of the MCOs' influence on the purchasing habits of their health plan subscribers.

MCOs often delegate the administration of the prescription benefits portion of their healthcare plan to a Prescription Benefits Manager ("PBM") in order to reduce administrative expenses. PBMs are private companies that contract with health plans or plan sponsors and specialize in claims processing and administrative functions involved with operating a prescription drug program. PBMs work to minimize costs and maintain profits through a variety of means, including volume purchases, quality control, formularies, movement of market share, and negotiated fees.

An MCO having charge of a number of healthcare facilities, such as nursing homes, will frequently negotiate a "national agreement" with a network of publicly held corporate pharmacies whereby all of the pharmacies within the PCP network agree to provide products and services to all of the healthcare facilities ("HCFs") owned by the MCO. The facilities may then purchase prescriptions from any of the PCP network pharmacies under the terms of the national agreement, often called a "plan." The MCO then outsources the administration of the plan to a PBM, which receives claims from PCP network pharmacies for each prescription filled for the MCO's healthcare facilities. The claims are reviewed by the PBM for compliance with the plan's terms.

The PBM may also perform ancillary services, such as ensuring compliance with a "formulary" system. A formulary is a list of drugs and treatment regimens deemed by a panel of healthcare professionals to be appropriate for treatment of various patient ailments. Formulary system management is the application of quantitative techniques to ensure high-quality, yet cost effective therapy. For example, a PBM may suggest an alternate drug regimen listed in the formulary having an equivalent efficacy as the originally prescribed drug but at a lower cost. Other services may include a Drug Utilization Review ("DUR") to ensure that patients are receiving appropriate, medically necessary, prescription drug therapy. Similarly, a Drug Regimen Review ("DRR") is a frequent evaluation of the medications being taken by a patient in intermediate- or long-term care facilities. Typically performed by a consulting or clinical pharmacist, DRR is especially useful in avoiding adverse drug reactions and drug interactions in patients taking multiple medications.

Problems can arise, however, when multiple facilities within a healthcare organization purchase prescriptions from multiple pharmacies within the PCP network. A frequent problem is non-uniform pricing of the same prescription by different pharmacies. Non-uniform pricing can occur for a number of reasons, such as misinterpretation of plan requirements and clerical errors. Another problem is inconsistent review of prescriptions for compliance to the plan formulary, which can easily result in a higher-cost therapy being dispensed. This causes the PBM to incur higher operating costs with little or no corresponding additional benefit to the patient. Still another problem is related to the pharmacies' DUR and DRR review of prescriptions. Inherent variations in operating practices for individual pharmacies in the network can lead to inconsistent review of prescriptions. These problems are exacerbated by the frequent geographic separation between the healthcare facilities, the pharmacies, and the PBM.

There is a need for a method to ensure that all prescriptions filled under a national contract are priced in accordance with the agreement. There is a further need to provide consistent formulary compliance under a national contract and to provide consistent review of prescriptions for adverse drug reactions.

SUMMARY

According to the present invention, a method is disclosed for providing consistent drug pricing and review of prescriptions within a national account. In accordance with this invention, a healthcare facility places an order for a prescription with a PCP network pharmacy participating in a prescription benefits management plan for the healthcare facility. The pharmacy receives the order and forwards a claim to a PBM processing center for review and adjudication. The processing center performs a review of the prescription for contractual and formulary compliance as defined by the healthcare facility's plan. A DUR and DRR review are also performed to ensure the appropriateness of the prescription for the patient. If no issues are detected, the pharmacy is notified and the order is filled and sent to the HCF. However, if any issues are found, the processing center notifies the pharmacy that the claim is rejected along with reasons for the rejection. The pharmacy then makes the necessary adjustments to resolve the issues and continues the claim process. A revised claim is then resubmitted to the processing center by the pharmacy and, if the issues have been adequately resolved (and no new issues have been raised), the pharmacy is issued an approval to fill the prescription and forward it to the HCF. If any issues remain, the pharmacy must continue to resolve them and resubmit the data to the processing center until all issues are resolved.

This method ensures that all healthcare facilities subscribing to a PBM and part of a national account, being serviced by various pharmacies within the PBM, are provided with consistent pricing, review, and adjudication of prescription claims. To facilitate timely processing of claims and prescriptions, an electronic communication network such as the Internet may be used to transmit and receive data.

An object of the present invention is a method for providing consistent processing of pharmacy data. An order for at least one prescription is transmitted from a healthcare facility to a pharmacy. The pharmacy receives the order and transmits a claim relating to the order from the pharmacy to a processing center. The processing center reviews the claim according to predetermined claim review criteria and accepts the claim only if it conforms to the claim review criteria. The processing center transmits one of an approval notification and a rejection notification from the processing center to the pharmacy. For accepted claims, the pharmacy fulfills the order, transmits the filled prescription from the pharmacy to the healthcare facility, and transmits an invoice corresponding to the filled prescription from the pharmacy to the healthcare facility. For rejected claims, the processing center transmits at least one basis for the rejection of the nonconforming claim to the pharmacy. The pharmacy corrects the non-conforming portion of the claim, then transmits the corrected claim to the processing center. The claim review and approval/fulfillment or rejection steps previously detailed are then repeated until the claim conforms to the predetermined claim criteria and the filled prescription and corresponding invoice are transmitted to the healthcare facility.

Another object of the present invention is an alternate method for providing consistent processing of pharmacy data. An order for at least one prescription is secured at a healthcare facility; and transmitted from the healthcare facility to a pharmacy by means of an electronic communication network. A claim relating to the order is transmitted from the pharmacy to a processing center by means of the electronic communication network. The claim is reviewed at the processing center by automatic means, according to predetermined claim review criteria. The claim is accepted only if it conforms to the claim review criteria. One of an approval notification and a rejection notification is transmitted from the processing center to the pharmacy by means of the electronic communication network. For accepted claims, the order is fulfilled at the pharmacy and the filled prescription is transmitted from the pharmacy to the healthcare facility. An invoice corresponding to the filled prescription is transmitted from the pharmacy to the healthcare facility by means of the electronic communication network. For rejected claims, at least one basis for the rejection of the nonconforming claim is transmitted from the processing center to the pharmacy by means of the electronic communication network. The non-conforming portion of the claim is corrected at the pharmacy. The corrected claim is transmitted from the pharmacy to the processing center by means of the electronic communication network. If any non-conformities remain, the claim is again rejected and the above steps are repeated until the claim conforms to the predetermined claim criteria and the filled prescription and corresponding invoice are transmitted to the healthcare facility.

Yet another object of the present invention is an alternate method for providing consistent processing of pharmacy data. An order for at least one prescription is transmitted from a healthcare facility to at least one pharmacy. The pharmacy transmits a claim relating to the order to a processing center. The processing center reviews the claim according to predetermined claim review criteria and accepts the claim only if it conforms to the claim review criteria. The processing center transmits one of an approval notification and a rejection notification to the pharmacy. For accepted claims, the pharmacy fulfills the order, transmits the filled prescription from the pharmacy to the healthcare facility, aggregates the accepted claim with other accepted claims for the healthcare facility, and periodically transmits an invoice for the aggregated claims from the pharmacy to the healthcare facility. For rejected claims, the processing center transmits at least one basis for the rejection of the nonconforming claim from the processing center to the pharmacy. The pharmacy corrects the non-conforming claim, then transmits the corrected claim to the processing center. The claim review and approval/fulfillment or rejection steps previously detailed are then repeated until the claim conforms to the predetermined claim criteria and the filled prescription is transmitted to the healthcare facility.

Still another object of the present invention is another method for providing consistent processing of pharmacy data. An order for at least one prescription is secured at a healthcare facility and transmitted from the healthcare facility to at least one pharmacy by means of an electronic communication network. A claim relating to the order is transmitted from the pharmacy to a processing center by means of the electronic communication network. The claim is reviewed at the processing center by automatic means, according to predetermined claim review criteria. The claim is accepted only if it conforms to the claim review criteria. One of an approval notification and a rejection notification is transmitted from the processing center to the pharmacy by means of the electronic communication network. For accepted claims, the order is fulfilled at the pharmacy and transmitted from the pharmacy to the healthcare facility. The accepted claim is aggregated with other accepted claims for the healthcare facility. For rejected claims, at least one basis for the rejection of the nonconforming claim is transmitted from the processing center to the pharmacy by means of the electronic communication network. The non-conforming claim is corrected at the pharmacy. The corrected claim is transmitted from the pharmacy to the processing center by means of the electronic communication network as previously detailed. The previously detailed steps are repeated until the claim conforms to the predetermined claim criteria and the filled prescription is transmitted to the healthcare facility. An invoice corresponding to the aggregated accepted claims is periodically transmitted from the processing center to the healthcare facility by means of the electronic communication network.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

Figure 1:
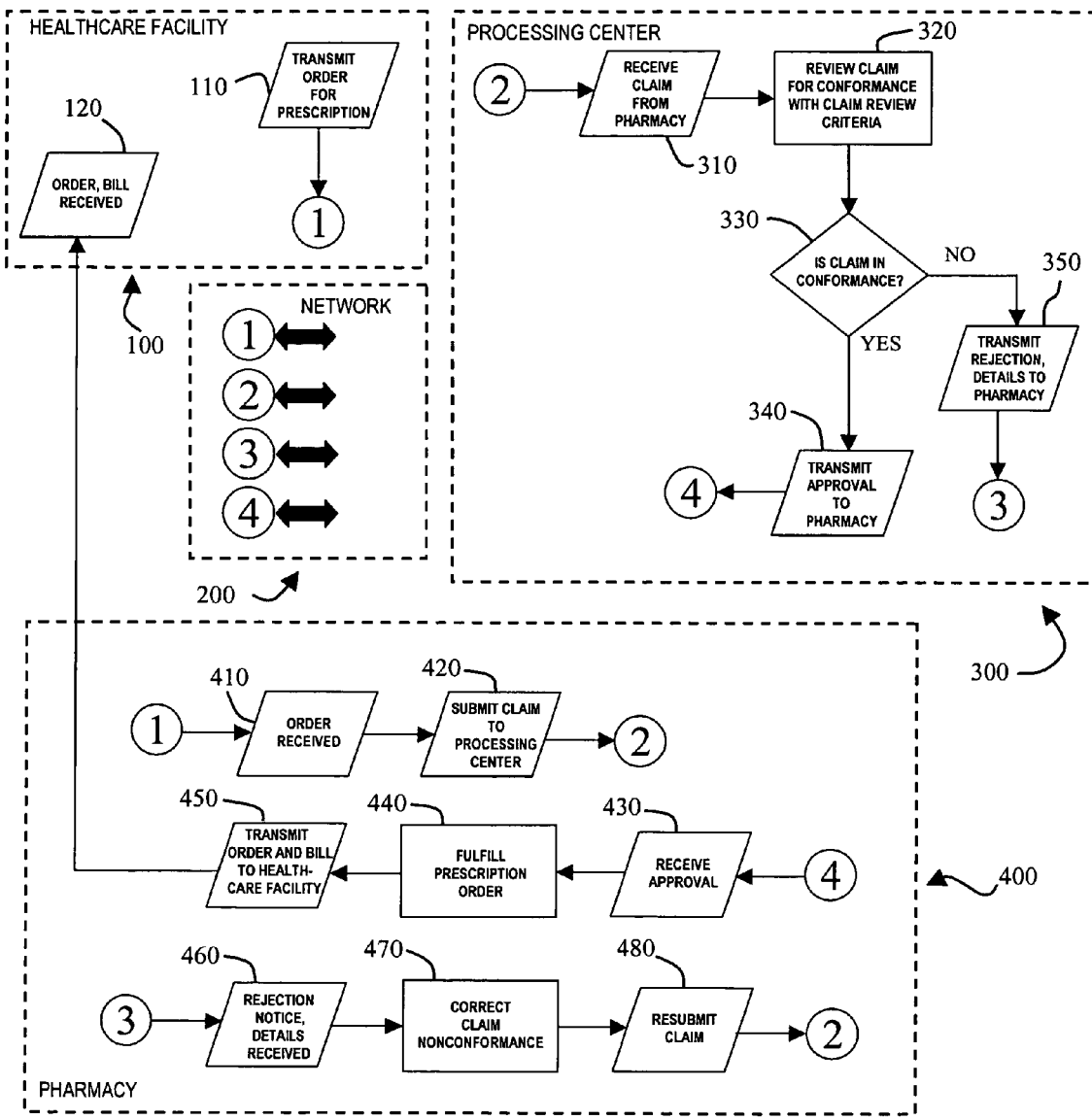
FIG. 1 is a block diagram of a method for processing pharmacy data according to an embodiment of the present invention.

A block diagram of a method for consistent processing of pharmacy data according to the invention is shown in FIG. 1. A healthcare facility 100 transmits an order for a prescription to a pharmacy 400 at step 110. The order may be transmitted to pharmacy 400 via an electronic communication network 200, such as an intranet or the Internet. The order may optionally be secured by any conventional means to ensure patient privacy and prevent tampering. Example means for securing the order include, without limitation, a Virtual Private Network ("VPN"), encryption, assigned usernames, passwords, digital signatures and digital certificates. Encryption methods include, but are not limited to, encryption methods based on the Data Encryption Standard ("DES") promulgated by the National Institute of Standards and Technology ("NIST") and Netscape's Secure Sockets Layer ("SSL"). An example digital signature standard is the Digital Signature Standard ("DSS") established by NIST. An example digital certificate standard is the ITU-T X509 international standard established by the International Telecommunications Union (ITU). The order may also be transmitted by conventional means, such as telephone, mail order, courier or facsimile.

Pharmacy 400 receives the prescription order at step 410, and transmits a claim relating to the order to a processing center 300 via the electronic communication network 200 at step 420. Processing center 300 receives the claim at step 310, and reviews the claim at step 320 for conformance to predetermined claim review criteria. The claim review criteria may include such items as contractual terms, patient information review, prescription price, formulary compliance with the healthcare facility's plan, and DRR and DUR reviews. The claim review is preferably automated, though a manual review may be conducted. An automated review may be accomplished by means of a predetermined set of instructions, such as a computer program.

If the claim is found to conform to the claim review criteria at step 330, an approval notification is transmitted to pharmacy 400 via the electronic communication network 200 at step 340. Pharmacy 400 receives the approval notification at step 430, fulfills the order at step 440, and transmits the order and invoice to HCF 100 at step 450. The filled prescription and invoice may be transmitted by any conventional means, such as mail, messenger, delivery service, or package carriers. HCF 100 receives the prescription and invoice at step 120. The invoice may be transmitted by means of electronic communication network 200 or in printed form.

However, if the claim is found to be nonconforming with regard to the predetermined review criteria at step 330, processing center 300 issues a rejection notification to pharmacy 400 and provides details regarding the basis for the rejection to the pharmacy at step 350. The rejection notification and/or rejection basis may be transmitted by means of the electronic communication network 200. Pharmacy 400 receives the rejection at step 460, corrects the claim criteria nonconformance at step 470, then resubmits the claim to processing center 300 at step 480. The resubmitted claim may be transmitted to processing center 300 via electronic communication network 200. The claim is then received and reviewed by processing center 300 at step 310 and subsequent steps. The process of steps 310, 320, 330, 350, 460, 470 and 480 is repeated as necessary until the claim conforms to the predetermined claim criteria and the prescription and invoice are transmitted to healthcare facility 100 in accordance with steps 340, 430, 440, 450 and 120.

Figure 2:
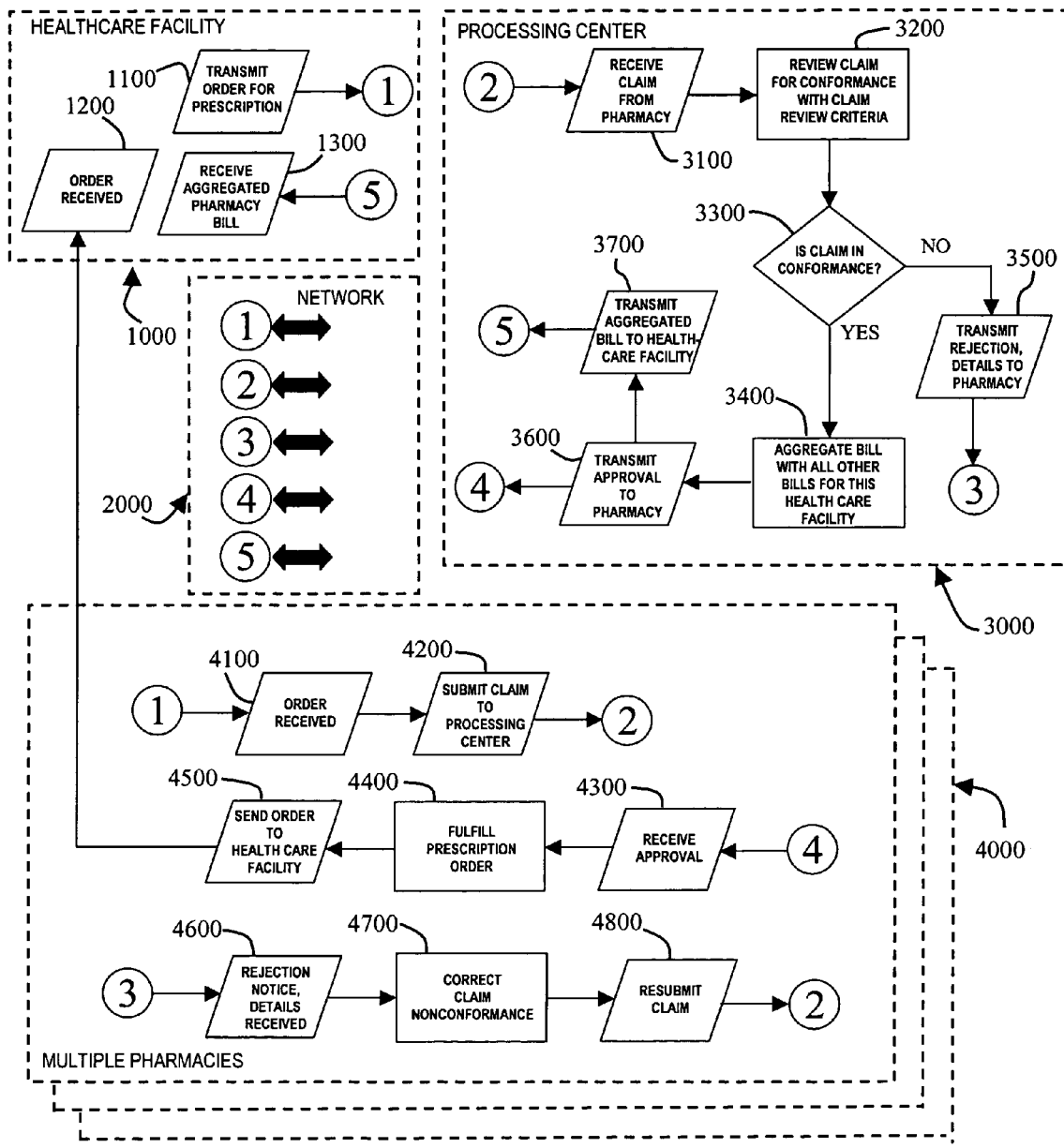
FIG. 2 is a block diagram of an alternate embodiment of a method for processing pharmacy data.

An alternate embodiment of the present invention is shown in FIG. 2. In this embodiment, a processing center 3000 provides a centralized billing or invoicing function wherein a healthcare facility 1000 purchases prescriptions from a plurality of pharmacies 4000. The pharmacies may be logically grouped, such as a chain or network, or may be independent pharmacies utilizing a common processing center 3000. Claims and billing information from the pharmacies are gathered by the processing center, adjudicated, and aggregated, resulting in a single invoice that is periodically sent to the HCF 1000 by processing center 3000. In the discussion that follows, the term "pharmacy" is intended to refer to any of the pharmacies utilizing processing center 3000.

A healthcare facility 1000 transmits an order for a prescription to a pharmacy at step 1100. The order may transmitted to one of multiple pharmacies 4000 via an electronic communication network 2000, such as an intranet or the Internet. The order may optionally be secured by any conventional means to ensure patient privacy and prevent tampering. Example means for securing the order include, without limitation, a Virtual Private Network ("VPN"), encryption, assigned user names, passwords, digital signatures and digital certificates. Encryption methods include, but are not limited to, encryption methods based on the Data Encryption Standard ("DES") promulgated by the U.S. National Bureau of Standards and Netscape's Secure Sockets Layer ("SSL"). An example digital signature standard is the Digital Signature Standard ("DSS") established by the National Institute of Standards and Technology (NIST). An example digital certificate standard is the ITU-T X509 international standard established by the International Telecommunications Union (ITU). Alternatively, the order may be transmitted by conventional means, such as telephone, mail order, courier or facsimile.

Pharmacy 4000 receives the prescription order at step 4100 and then transmits a claim relating to the order to a processing center 3000 via the electronic communication network 2000 at step 4200. Processing center 3000 receives the prescription claim at step 3100 and reviews the claim at step 3200 for conformance to predetermined claim review criteria. The claim review criteria may include such items as contractual terms, patient information review, prescription price, formulary compliance with the HCF's plan, and DRR and DUR reviews. The claim review is preferably automated, but may optionally be conducted manually. An automated review may be accomplished by means of a predetermined set of instructions, such as a computer program.

If the claim is found to conform to the claim review criteria at step 3300, processing center 3000 aggregates at step 3400 the accepted claim with accepted claims from other pharmacies 4000 that have also provided products to healthcare facility 1000. An approval notification is transmitted to pharmacy 4000 via electronic communication network 2000 at step 3600.

Pharmacy 4000 receives the approval notification at step 4300, fulfills the prescription order at step 4400, and then transmits it to HCF 1000 at step 4500. The filled prescription may be transmitted by any conventional means, such as mail, messenger, delivery service or package carriers. HCF 1000 then receives the prescription at step 1200.

However, if the claim is found to be nonconforming with regard to the predetermined review criteria at step 3300, processing center 3000 issues a rejection notification to pharmacy 4000 at step 3500 and provides details regarding the basis for the rejection. The rejection notification and/or rejection basis may be transmitted by means of electronic communication network 2000. Pharmacy 4000 receives the rejection at step 4600, takes appropriate measures to correct the claim criteria nonconformance at step 4700, then resubmits the claim to processing center 3000 at step 4800. The resubmitted claim may be transmitted to processing center 3000 via electronic communication network 2000, where it is then reviewed by the processing center at step 3100 and subsequent steps. The process of steps 3100, 3200, 3300, 3500, 4600, 4700 and 4800 is repeated as necessary until the claim conforms to the predetermined claim criteria and the prescription is transmitted to healthcare facility 1000 in accordance with steps 3400, 3600, 4300, 4400, 4500 and 1200.

Processing center 3000 periodically sends healthcare facility 1000 an invoice at step 3700 reflecting charges for all of the accepted claims aggregated at step 3400. The invoice may be transmitted electronically via electronic communication network 2000 or in a printed form.

This embodiment of the present invention also offers the ability for the PBM 3000 to provide the healthcare facility 1000 and its corporate parent a number of reports, such as quality assurance, formulary compliance and "roll-ups" (i.e., aggregation and summarization) of DRR and DUR.

The present invention provides a number of advantages to each class of participant in the managed care system. The online communications between the PBM processing center and the participating pharmacies enable the pharmacies to obtain rapid feedback regarding the prescription's pricing and therapeutic appropriateness for the patient. The pharmacies also benefit from the reduced time required to ensure plan compliance and make corrections. The patient benefits from the PBM's DUR and DRR reviews, avoiding potentially harmful drug reactions and interactions. The patient also benefits indirectly from the PBM's cost-containment activities, which serve to minimize health-care plan increases. Lastly, the MCO benefits from the PBM's cost-containment procedures and increased subscriber satisfaction.

While this invention has been shown and described with respect to a detailed embodiment thereof, it will be understood by those skilled in the art that various changes in form and detail thereof may be made without departing from the scope of the claims of the invention.

What is claimed is:

1. A method of using a computer to provide consistent drug pricing and medication prescription review for a plurality of pharmacies within a pharmacy network that have a contractual relationship with a managed care organization, the method comprising the steps of:

transmitting a first medication prescription order over a communication network by a healthcare facility computer to a first pharmacy computer of a first of the plurality of pharmacies, wherein the healthcare facility is affiliated with a managed care organization ("MCO");

transmitting a second medication prescription order over the communication network by the healthcare facility computer to a second pharmacy computer of a second of the plurality of pharmacies;

transmitting a first claim relating to the first medication prescription order over the communication network by the first pharmacy computer to a processing center computer of a prescription benefits manager contracted with the MCO;

transmitting a second claim relating to the second medication prescription order over the communication network by the second pharmacy computer to the processing center computer;

reviewing the first and second claims by the processing center computer according to predetermined claim review criteria for the drug pricing and the respective medication prescriptions;

if either of the claims conform to the predetermined claim review criteria:

transmitting over the communication network an approval notification for the respective claim by the processing center computer to the respective pharmacy computer, fulfilling the order for the respective prescription at the respective pharmacy, sending the fulfilled order from the respective pharmacy to the healthcare facility, and otherwise:

transmitting a rejection notification and at least one basis for the rejection of the nonconforming claim over the communication network by the processing center computer to the respective pharmacy computer, correcting the non-conforming portion of the non-conforming claim at the respective pharmacy, transmitting the corrected claim over the communication network by the respective pharmacy computer to the processing center computer, repeating the step of reviewing the claim until the claim conforms to the predetermined claim criteria, and sending a filled respective prescription from the respective pharmacy to the healthcare facility;

aggregating by the processing center computer a plurality of approved claims for each of the filled respective prescriptions, wherein the plurality of approved claims are aggregated for the healthcare facility; and transmitting an invoice for the aggregated claims over the computer network by the processing center computer to the healthcare facility computer.

2. The method according to claim 1, further comprising the step of securing the first prescription order and the second prescription order prior to transmitting the orders to the respective pharmacy computer.

3. The method according to claim 1 wherein the respective claim reviews are accomplished automatically in accordance with predetermined review criteria.

4. The method according to claim 1, further comprising the steps of:

preparing at least one report relating to the respective orders and respective claims; and transmitting the report over the communication network by the processing center computer to the healthcare facility computer.

\* \* \* \* \*